(12) United States Patent
Nemec et al.

(10) Patent No.: US 7,241,298 B2
(45) Date of Patent: Jul. 10, 2007

(54) UNIVERSAL ALIGNMENT GUIDE

(75) Inventors: Mark Nemec, Chester, NY (US); Mike Cusick, Warwick, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 354 days.

(21) Appl. No.: 10/356,255

(22) Filed: Jan. 31, 2003

(65) Prior Publication Data

US 2004/0153083 A1 Aug. 5, 2004

(51) Int. Cl.
  *A61F 5/00* (2006.01)
  *A61B 17/58*
(52) U.S. Cl. .......................... 606/86; 606/88
(58) Field of Classification Search .............. 606/86, 606/87, 88, 89, 96, 97, 98, 102, 62, 130
  See application file for complete search history.

(56) References Cited

U.S. PATENT DOCUMENTS

| | | | |
|---|---|---|---|
| 3,457,922 A | 7/1969 | Ray | |
| 4,703,751 A | 11/1987 | Pohl | |
| 4,809,694 A * | 3/1989 | Ferrara | 606/130 |
| 4,952,213 A | 8/1990 | Bowman et al. | |
| 5,263,956 A * | 11/1993 | Nobles | 606/130 |
| 5,279,575 A | 1/1994 | Sugarbaker | |
| 5,342,368 A | 8/1994 | Petersen | |
| 5,364,401 A | 11/1994 | Ferrante et al. | |
| 5,375,588 A | 12/1994 | Yoon | |
| 5,443,464 A * | 8/1995 | Russell et al. | 606/54 |
| 5,514,139 A | 5/1996 | Goldstein et al. | |
| 5,597,379 A | 1/1997 | Haines et al. | |
| 5,643,272 A | 7/1997 | Haines et al. | |
| 5,658,272 A | 8/1997 | Hasson | |
| 5,681,316 A | 10/1997 | DeOrio et al. | |
| 5,690,632 A | 11/1997 | Schwartz et al. | |
| 5,755,803 A | 5/1998 | Haines et al. | |
| 5,810,712 A | 9/1998 | Dunn | |
| 5,810,827 A | 9/1998 | Haines et al. | |
| 5,879,354 A | 3/1999 | Haines et al. | |
| 6,056,754 A | 5/2000 | Haines et al. | |
| 6,110,182 A | 8/2000 | Mowlai-Ashtiani | |
| 6,190,395 B1 | 2/2001 | Williams | |
| 6,195,577 B1 | 2/2001 | Truwit et al. | |
| 6,197,064 B1 | 3/2001 | Haines et al. | |
| 6,206,890 B1 | 3/2001 | Truwit | |
| 6,258,095 B1 | 7/2001 | Lombardo et al. | |
| 6,267,769 B1 | 7/2001 | Truwit | |
| 6,267,770 B1 | 7/2001 | Truwit | |
| 6,306,146 B1 * | 10/2001 | Dinkler | 606/130 |
| 6,385,475 B1 | 5/2002 | Cinquin et al. | |
| 6,579,281 B2 | 6/2003 | Palmer et al. | |

(Continued)

FOREIGN PATENT DOCUMENTS

| | | |
|---|---|---|
| DE | 202 02 615 U1 | 6/2002 |
| EP | 0 469 966 A1 | 2/1992 |
| EP | 0 490 812 A1 | 6/1992 |
| EP | 1 442 712 A | 8/2004 |
| WO | WO-94/00066 A1 | 1/1994 |
| WO | 2004/017843 A | 3/2004 |

*Primary Examiner*—Pedro Philogene
(74) *Attorney, Agent, or Firm*—Lerner, David, Littenberg, Krumholz & Mentlik, LLP

(57) ABSTRACT

A universal alignment guide for universally positioning an instrument with respect to a bone to facilitate resecting the bone along desired orientations. The alignment guide comprises a spheroidal base and a collar coupled to the base in a manner to allow universal motion of the collar with respect to the base. The base of the alignment guide is attached to a bone anchor implanted in a bone, and the collar is attached to an instrument, such as a resection guide. With respect to a distal femur, the alignment guide facilitates simultaneous positioning and locking of the resection guide in flexion/extension, varus/valgus, internal/external rotation, and proximal/distal orientations.

30 Claims, 6 Drawing Sheets

U.S. PATENT DOCUMENTS

| | | |
|---|---|---|
| 6,595,997 B2 * | 7/2003 | Axelson et al. ............... 606/88 |
| 6,695,848 B2 | 2/2004 | Haines |
| 7,029,477 B2 * | 4/2006 | Grimm ........................ 606/88 |
| 2002/0107522 A1 | 8/2002 | Picard et al. |
| 2002/0133160 A1 | 9/2002 | Axelson et al. |
| 2002/0133163 A1 | 9/2002 | Moctezuma et al. |
| 2003/0040753 A1 | 2/2003 | Daum et al. |
| 2003/0055436 A1 | 3/2003 | Daum et al. |
| 2003/0069591 A1 | 4/2003 | Carson et al. |
| 2003/0171757 A1 | 9/2003 | Coon et al. |
| 2004/0039396 A1 | 2/2004 | Couture et al. |
| 2004/0122436 A1 | 6/2004 | Grimm |

* cited by examiner

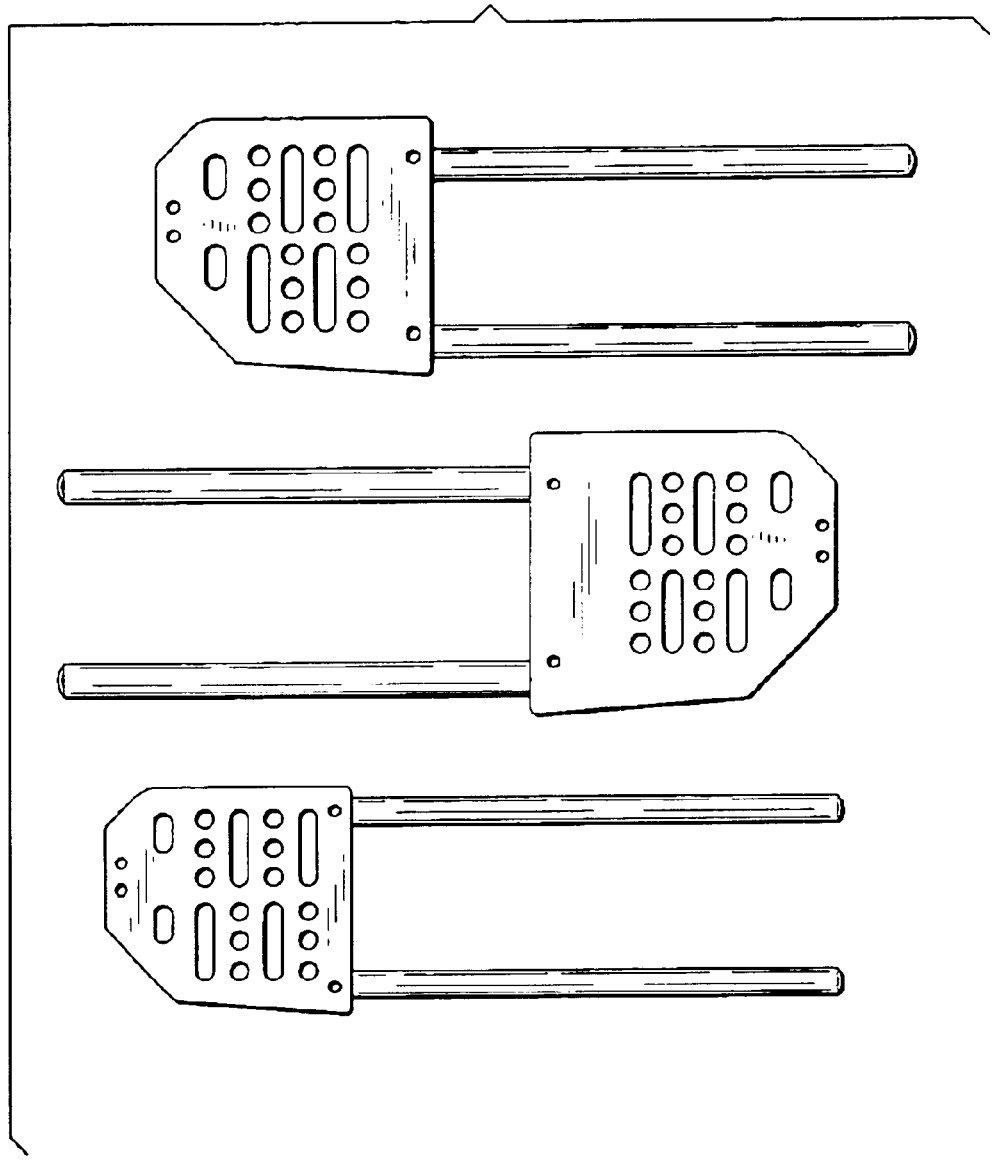

UNIVERSAL ALIGNMENT GUIDE

BACKGROUND OF THE INVENTION

1. Field of the Invention

The invention relates to methods and instrumentation for use in preparing a bone surface for attachment of a prosthesis. More particularly, the invention relates to methods and instrumentation for aiding in the alignment and positioning of a resection guide relative to bone surfaces, in order to resect the bone surfaces and prepare them for attachment of endoprostheses. A common procedure in which this invention may be employed is knee arthroplasty.

2. Brief Description of the Prior Art

Joint replacement procedures, such as total knee arthroplasty, involve replacement of the load bearing surfaces of bones with artificial components. Proper implantation of these components, or implants, requires detailed measurements of the joint as well as accurate resections of the bone surfaces in preparation for their attachment to their respective components.

As used herein, when referring to bones or other body parts, the term "proximal" means closest to the heart, and the term "distal" means more distant from the heart. When referring to tools and instruments, the term "proximal" means closest to the practitioner, and the term "distal" means distant from the practitioner.

In attempting to duplicate the natural behavior of the joint, replacement components require specific positioning and attachment to the bones of the joint that they are to replace, in accordance with the detailed measurements. Commonly, since the bone-contacting surface of an implant, for example a distal femoral component, has a specific geometry, the bone to which it is to be attached must be accurately resected and shaped to mate with the geometry of the implant and provide the implant's proper alignment in the joint.

Measurement and placement of the distal femoral component, for example, requires determination of the following four orientations prior to implantation: proximal/distal, flexion/extension, varus/valgus, and internal/external rotation.

Various techniques and instruments are known for facilitating making these measurements and then resecting the bone surfaces accordingly. Examples of such are found in published U.S. patent application Ser. Nos. 20020133160, 20020133161, 20020133162 and 20020133163, as well as U.S. patent application Ser. No. 09/974,524, entitled "Methods and Tools for Femoral Resection in Knee Surgery". These applications teach an alignment guide coupled to a bone anchor that is attached to the distal femur. The alignment guide is also joined to a resection guide via an attachment rod. Orientation and locking of the resection guide is done via three cam locks on the alignment guide. One cam lock is for adjusting and locking varus/valgus orientation, another is for flexion/extension, and a third is for proximal distal orientation of the resection guide relative to the distal femur. This alignment guide is therefore designed for independent locking of three orientation positions of the resection guide. Removal of the resection guide and attachment of further instruments would provide additional positioning capabilities.

Recently, various computerized systems have been introduced to aid the practitioner during different surgical procedures. These systems include multiple video cameras which are deployed above the surgical site and a plurality of dynamic reference frame (DRF) devices, also known as trackers, which are attached to body parts and surgical instruments. The trackers are generally LED devices which are visible to the cameras. Using software designed for a particular surgical procedure, a computer receiving input from the cameras guides the placement of surgical instruments.

Additionally, computer-assisted surgery has been developed which utilizes a tracking system that can relate positions on the patients and/or instruments to stored X-ray, CT scan and MRI data previously obtained for the patient. More recently, image free computer-aided surgery has been utilized where mechanical relationships can be calculated from anatomical reference points such as in joint arthroplasty. These systems are used intra-operatively for performing various surgical procedures, including replacement of artificial joints.

It has been especially useful to utilize trackable medical instruments for use in procedures utilizing computer-assisted image guided or image free medical and surgical navigation systems. Systems using body images are shown in U.S. Pat. Nos. 5,383,454 to Bucholz and 6,021,343 to Foley et al. In general, these image-guided systems use computer stored digital images of a body part obtained, for example, by CT scans taken before surgery, to generate images on a display, such as a CRT monitor screen, during surgery. These images are used in connection with real time information for representing the position of a surgical instrument with respect to the body part. The systems typically include tracking devices such as, for example, a tracker having LEDs and attachable to a surgical instrument as well as a patient's body part, a tracking array used in real time during surgery to track the position of the body part and the instrument via the tracker, and a monitor screen to display images representing the body and the position of the instrument relative to the stored images as the surgical procedure is performed.

An image-free type system is shown in U.S. Pat. No. 6,385,475. Some systems of this type include virtual joint images. In such systems, active or passive marker elements are attached to bones on opposite sides of a joint and a measuring device, such as an optical sensing camera coupled to a data processing system to which signals corresponding to the positioning data of the marker elements is supplied by the optical camera system, is used to correlate the markers on opposite sides of the joint. With a pointer mounted tracker, it is possible to locate various anatomic reference points on the joints to allow the system to position a cutting instrument such as a reamer or saw blade.

The prior art instrumnts used for determining the correct orientations for tibial and femoral resection in total knee arthroplasty, for example, leave room for optimization with respect to their designs, interaction with computer-assisted surgery instrumentation, as well as speed and ease of use.

SUMMARY OF THE INVENTION

It is an object of the present invention to provide an instrument which facilitates the determination and setting of numerous desired alignment orientations respective to a bone. With reference to a distal femur, for example, these are referred to as proximal/distal, flexion/extension, varus/valgus, and internal/external rotation. Those skilled in the art will recognize that comparable movements and orientations on other bone segments, although termed differently, will be similarly facilitated by the present invention.

It is also an object of the present invention to provide an instrument which facilitates the determination and setting of numerous desired orientations simultaneously, rather than sequentially.

It is yet another object of the present invention to provide an improved instrument design that offers greater speed and ease of use.

These and other objects are achieved by the present invention, which is a universal alignment guide for positioning an instrument with respect to a bone.

In the preferred embodiment, the alignment guide is comprised of a spheroidal base and a collar associated with the base in such manner as to facilitate universal motion of the collar with respect to the base. The base is attached to one end of a bone anchor, the bone anchor being set in a bone at its other end. It is noted that the spheroidal base need not be a full sphere, but only enough of a structure to facilitate the universal motion between the collar and the base, as described herein.

In a second embodiment, the collar, rather than the base, is associated with the bone anchor, leaving the base free to move with respect to the collar. With regard to this embodiment, the description of features of other embodiments, as well as the preferred embodiment, may be similarly incorporated into this second embodiment.

It is noted that the bone anchor may be set at any convenient location on any desired bone. For example, the anchor may be set medially or laterally on the distal femur, or on the humeral head. Advantageously, the anchor is positioned so as to facilitate unencumbered positioning and use of the alignment guide and resection guide, as well as any other instruments, trial components, and implants. Also advantageously, the anchor is set three inches from the end of the distal femur. Additionally, the anchor may be attached to the bone in a variety of ways commonly known to those skilled in the art. Some non-limiting examples of attachment are screwing, clamping or cementing the anchor to the bone.

In the preferred embodiment, a resection guide may be attached to the freely movable collar, for universal positioning with respect to the bone. Alternatively, in the second embodiment, the resection guide may be attached to the freely movable base for the same purpose. As commonly known to those skilled in the art, the resection guide is used to facilitate cutting the bone at desired orientations. The attachment and manipulation of other cutting guides and instruments, however, is also envisioned, and is encompassed generally by reference to the term resection guide, as used herein.

In the preferred embodiment, the collar is advantageously assembled from a top and bottom portion. These two portions are positioned so as to encapsulate the spheroidal base, and are then joined together. The preferred method of joining the two portions together is by shielded metal arc welding (SMAW). It is recognized, however, that there are many other methods, techniques and designs to facilitate joining the two portions of the collar together.

In the preferred embodiment, the base contains a through bore, or passage, for cooperative assembly with one end of the bone anchor. In a third embodiment, not shown, the passage terminates inside the base, rather than penetrating all the way through. In the second embodiment, the collar contains at least one passage for cooperative assembly with one end of the bone anchor.

In the preferred embodiment, once the bone anchor is inserted into the passage in the base, in order to lock the base against the bone anchor, a threaded slot in the base, together with an accompanying fixator, or set screw, are provided. The slot intersects with the passage, and the set screw is forwarded through the slot until it abuts the bone anchor, thus stabilizing and locking the base in position against the bone anchor. An opening, or window, is further provided in the collar of the alignment guide to allow additional access to the set screw. In the second embodiment, this is similarly accomplished, except with the bone anchor being inserted into a passage in the collar.

In the preferred embodiment, on the portion of the base facing the bone, is a flattened surface to enable closer positioning of the base, and consequently, the alignment guide, to the bone.

Further in the preferred embodiment, the collar contains a motion governor which facilitates locking the collar against the base once the desired position of the collar relative to the bone has been selected. The motion governor is made up of an actuator, or threaded knob, and a threaded aperture in the collar. Preferably, the threaded aperture is located in a protrusion on the collar. Among other advantages, the protrusion provides added surface area to the aperture for increased threaded engagement between the knob and collar. The second embodiment contains similar structure.

In the preferred embodiment, locking of the collar against the base is accomplished in the same manner as locking the base against the bone anchor. That is, the threaded knob is advanced through the aperture in the collar until the knob abuts the base and locks the collar in position against the base.

In the preferred embodiment, the alignment guide further contains a resection guide. The resection guide has two attachment rods which slidably engage two channels in the collar. It is possible, however, that the resection guide, or any other attaching instrument, may be coupled to the alignment guide via at least one area of contact.

Preferably, the channels and rods of the resection guide have rounded circumferences, however, any geometry may be implemented. Also preferably, the channels are located in protrusions on the collar, which provide added material to the collar to support assembly and interaction with the resection guide.

In the preferred embodiment, each of thee protrusions on the collar also contains at least two threaded bores. On each protrusion, the bores are oriented at ninety degrees to each other as well as to the channel. Each bore accepts an arrestor, or threaded knob. It is also envisioned, however, that a protrusion may have at least one bore, and that the angularity of a bore relative to either another bore, or to a channel, may be other than ninety degrees.

In the preferred embodiment, upon insertion of both attachment rods of the resection guide into the respective channels in the collar, each one of two knobs, when advanced through a selected bore on oppositely oriented protrusions of the collar, is used to lock the resection guide in place. It is noted that having two bores oriented at ninety degrees to each other on one protrusion, advantageously provides an additional angle of insertion of the knobs for locking the attachment rods of the resection guide against the collar.

The preferred method of using the present invention includes attaching a bone anchor to a bone such as a femur or humerus, coupling the base of the alignment guide to the bone anchor, locking the base against the anchor to prevent it's movement with respect to the bone, attaching a resection guide to the collar, orienting the resection guide relative to the bone by movement of the collar relative to the bone, and fixing the desired position of the resection guide by locking the collar against the base with an actuator and locking the resection guide in the collar with arrestors.

With reference to the distal femur, and without regard to the particular instrument attached to the alignment guide, in the preferred embodiment, the orientations of flexion/extension, varus/valgus and internal/external rotation are accomplished by moving the collar relative to the base. Proximal/distal orientation is accomplished by moving the resection guide relative to the collar.

It is preferable to first set all of the desired orientations and then lock the collar and resection guide in place. However, locking the collar and resection guide sequentially is also possible.

The present invention may be used by itself, or in conjunction with other navigational equipment such as a computer-aided surgery system using an optical tracking system mounted on the instrument, which aids in the location and positioning of various resection planes relative to a bone.

BRIEF DESCRIPTION OF THE DRAWINGS

In the drawings, wherein similar reference characters denote similar elements throughout the several view:

FIG. 8. is a perspective view of a set of variously sized lateral cutting blocks.

DETAILED DESCRIPTION

Figure 1:
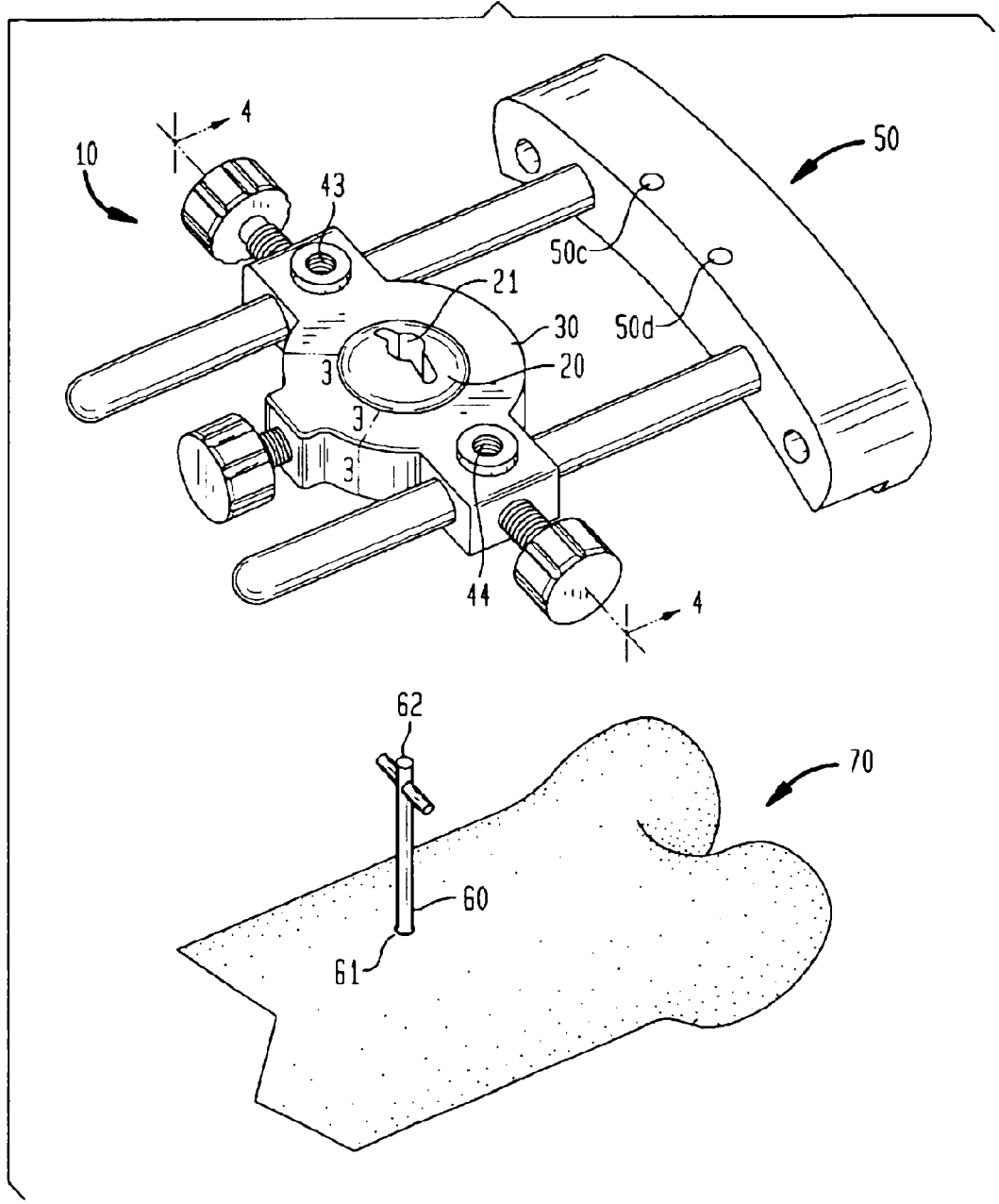
FIG. 1 is an exploded view of the universal alignment guide attached to a resection guide, where the base is attachable to a bone anchor implanted at one of its ends in the distal femur.
Figure 2:
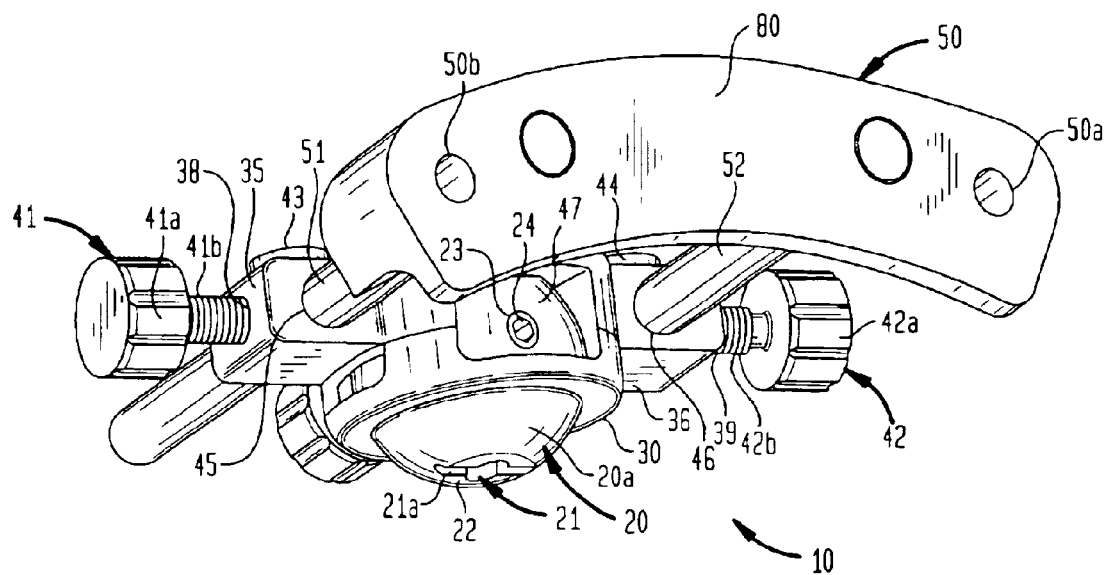
FIG. 2 is a perspective view of the side of the universal alignment guide facing the distal femur, with a resection guide attached.

Referring to FIGS. 1 and 2, there is illustrated the preferred embodiment of the universal alignment guide of the present invention, generally denoted as 10, with a bone resection guide 50 attached. The alignment guide is positioned over a bone anchor 60 that is implanted into the distal femur 70.

Figure 7:
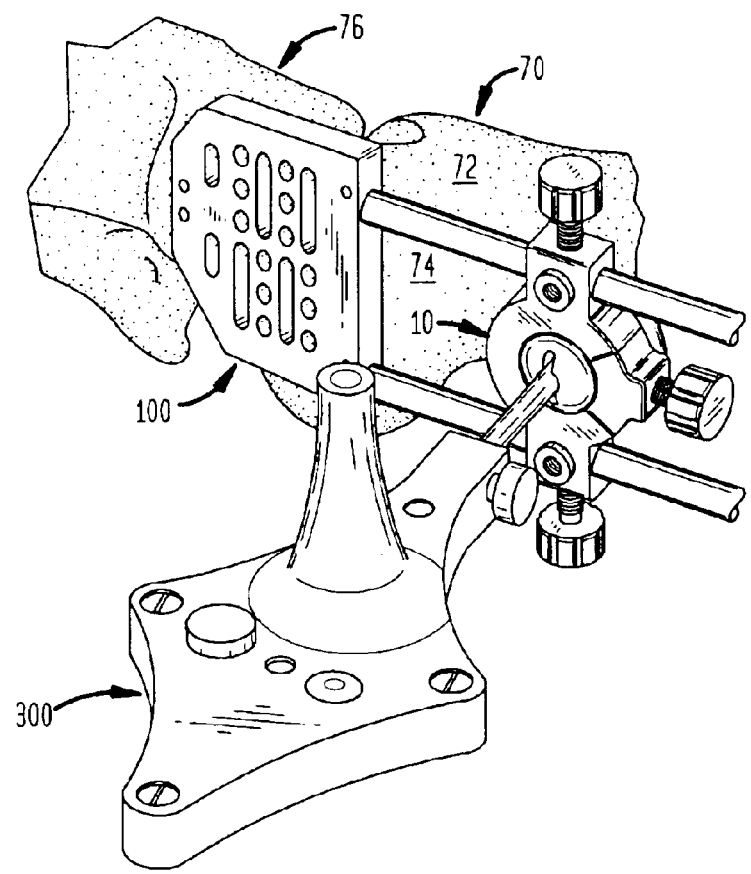
FIG. 7. is a perspective view of the alignment guide, lateral resection guide, and tracker in a lateral orientation with respect to the knee joint.

Initially, bone anchor 60, having a first end 61 and a second end 62, is implanted at its first end 61 into the anterior portion of distal femur 70. In the preferred embodiment, the configuration of second end 62 of bone anchor 60 includes a cross-bar 63 which engages a slot 21a in passage 21 of spheroidal base 20, and facilitates proper mating with alignment guide 10. Additionally, cross-bar 63 serves as an attachment point for a tracker 300, as shown in FIG. 7. It is recognized that various other designs of second end 62 of bone anchor 60 may suffice for these purposes.

Referring to FIG. 2 where the side of alignment guide 10 facing distal femur 70 is depicted for better visibility of structures, alignment guide 10 has a spheroidal base 20. Base 20 has an outer spherical surface 20a and a diameter of preferably one inch, although other dimensions are envisioned. Base 20 also has an advantageously flattened surface 22 on the side facing distal femur 70 to allow it to be positioned closer to the bone. It is noted that base 20 need not be a full sphere, but only enough of a structure to facilitate the universal motion between collar 30 and base 20, as described herein.

In the preferred embodiment, base 20 has passage, or bore, 21 into which bone anchor 60 is inserted. In an alternate embodiment, not shown, passage 21 may terminate inside base 20. In the preferred embodiment, passage 21 has a cross-slot 21a such that it will accept and mate with cross-bar 63 of second end 62 of bone anchor 60. Base 20 further has a threaded slot 23 which is oriented on base 20 so that it intersects passage 21. Once the second end 62 of bone anchor 60 is inserted into passage 21 in base 20 of alignment guide 10, a fixator, or set screw 24, is threaded into slot 23 and advanced until it abuts bone anchor 61 in passage 21. Tightening of set screw 24 against bone anchor 60, secures base 20 against bone anchor 60.

Figure 3:
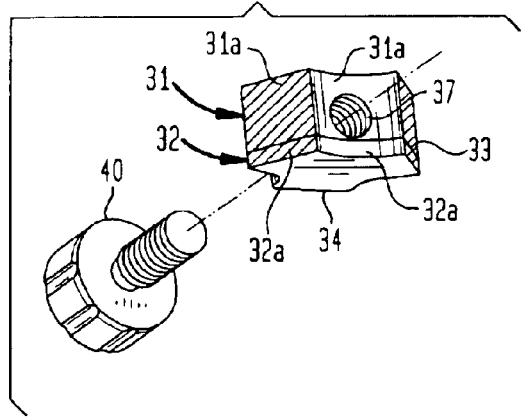
FIG. 3 is an exploded view of the rear section of the universal alignment guide cut away along lines 3—3 of FIG. 1.

In the preferred embodiment, alignment guide 10 also has a collar 30 that partially encapsulates base 20, thereby facilitating universal motion of collar 30 with respect to base 20. As seen in FIG. 3, collar 30 is formed of two halves that are joined together. The inner surfaces 31a and 32a of collar 30 match the outer spherical surface 20a of base 20 for sliding engagement therewith. Top portion 31 and bottom portion 32 are initially positioned on either side of base 20, brought into contact with each other, and then welded by shielded metal arc welding (SMAW). It is understood that there are many other variations and configurations possible for assembling collar 30 around base 20. Additionally, it is noted that collar 30 advantageously has a window 47 that provides added access to slot 23 in the base 20 for adjustment of set screw 24 in slot 23.

Referring to FIGS. 2 and 3, in the preferred embodiment, collar 30 has three protrusions 34, 35, 36. Protrusion 34 has one threaded opening, or aperture, 37 leading to base 20, while protrusions 35 and 36 each have three orthogonal openings. More specifically, protrusion 35 has two orthogonal threaded bores 38 and 43, and channel 45. Similarly, protrusion 36 has two orthogonal threaded bores 39 and 44, and channel 46. Although depicted as a knob, or actuator, 40, threadably cooperating with bore 37, and knobs, or arrestors, 41 and 42, threadably cooperating with bores 38 and 39 respectively, it is understood that bores 37, 38, 39, 43 and 44 are similarly threaded and accommodate knobs 40, 41 and 42 interchangeably. In the preferred embodiment, knobs 40, 41 and 42 have textured knob heads 40a, 41a and 42a, and threaded shafts 40b, 41b and 42b. The use of protrusions 34, 35 and 36, as well as bores 37, 38, 39, 43 44, and knobs 40, 41 and 42 will be explained in more detail below.

As mentioned above, protrusions 35 and 36 contain channels 45 and 46 that penetrate protrusions 35 and 36 respectively. These channels 45, 46 are designed for engagement with resection guide 50.

Figure 6:
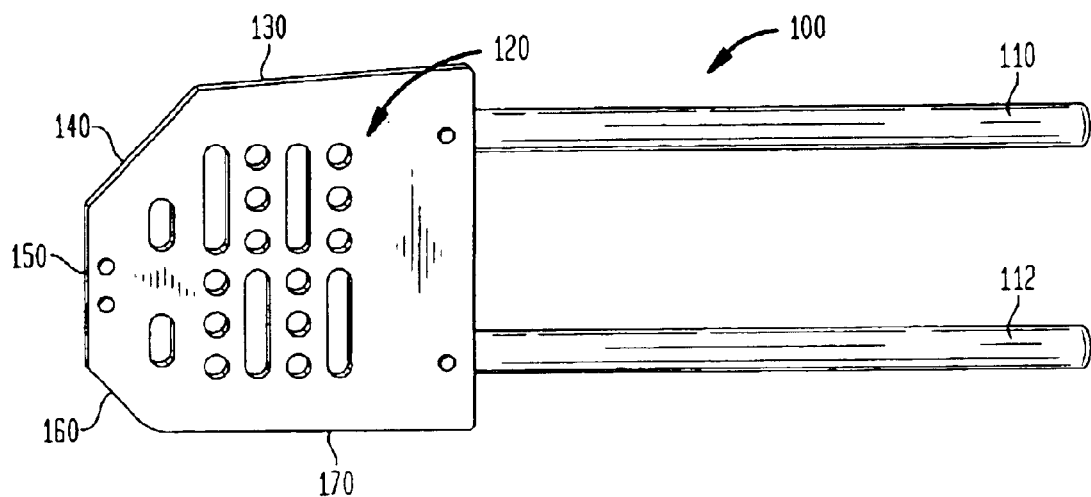
FIG. 6 is a side view of a lateral cutting block used in conjunction with the lateral approach for knee replacement surgery.

Resection guide 50 has first and second attachment rods 51 and 52 which slidably engage respective channels 45 and 46 in protrusions 35 and 36 of collar 30. It is recognized that although the cross-sections of channels 45, 46 and rods 51, 52 are round, any interactive shapes and configurations are possible. Resection guide 50 also includes rotatable pin guides 50a and 50b to facilitate joining other surgical instruments to resection guide 50, as well as attachment points 50*c* and 50*d* for use in connecting trackers, such as tracker 300 depicted in FIG. 7, to resection guide 50. Another embodiment of a resection guide is shown in FIGS. 6–8 as lateral resection guide 100, and will be discussed in more detail, below.

Protrusions 34, 35 and 36 provide added material to the collar for interaction with knobs 40, 41 and 42 of resection guide 50. However, it is also envisioned that collar 30 may be made without protrusions by uniformly having more circumferential material to support and interact with knobs 40, 41, and 42 and resection guide 50.

In operation, once rods 51, 52 of resection guide 50 are inserted into their respective channels 45, 46, knobs 41 and 42 are used to lock resection guide 50 in place. This is done, for example, by threadably forwarding knob 41 through bore 38 until knob 41 abuts rod 51 of resection guide 50 within protrusion 35, thereby locking resection guide 50 in place with respect to collar 30. Although it is recognized that one knob will lock resection guide 50 in place, preferably, a second knob, 42 can also be threadably advanced through bore 38 until it abuts rod 52 in channel 46, thereby more securely locking resection guide 50 to collar 30 of alignment guide 10. It is further recognized that resection guide 50 may have only one attachment rod, and be attached and locked to collar 30 via only that rod.

Figure 4:
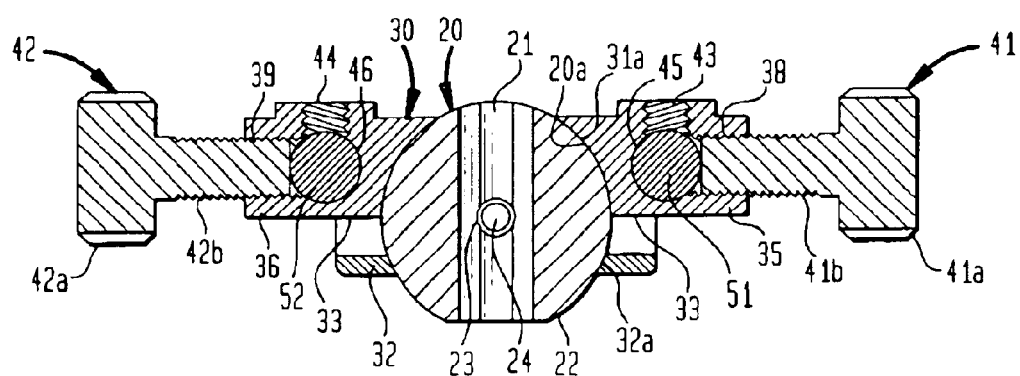
FIG. 4 is a frontal section view of the alignment guide cut away along lines 4—4 in FIG. 1.

Referring to FIGS. 1, 2 and 4, on protrusion 35, bores 38, 43, and channel 45 are oriented at ninety degrees to each other, and on protrusion 36, bores 39, 44 and channel 46 are similarly oriented at ninety degrees to each other. The purpose for additional bores 43 and 44 is to afford additional angles of engagement of rods 51 and 52 of resection guide 50 by knobs 41 and 42. This is useful, for example, when intraoperatively, there may be insufficient room, or it may be inconvenient, for inserting knob 41 through bore 38. Consequently, knob 41 may be alternatively inserted through bore 43 to lock the resection guide 50 in place.

The components of alignment guide 10 are preferably made from surgical grade materials. In the preferred embodiment, base 20, collar 30, set screw 24 as well as knob heads 40*a*, 41*a*, and 42*a* and knob shafts 40*b*, 41*b*, and 42*b* are made from surgical grade stainless steel. Other surgical grade materials, as well as disposable materials are, of course, also envisioned.

In conjunction with the preferred embodiment depicted in FIGS. 1–4, the following is the preferred procedure for using universal resection guide 10. Although illustrative, and while remaining within the spirit of the present invention, it is understood by those skilled in the art that these steps need not necessarily all be performed in sequence.

First, bone anchor 60 is implanted into the anterior surface of distal femur 70 approximately three inches away from the end of the distal femur. As mentioned previously, advantageously, the anchor is positioned so as to facilitate unencumbered positioning and use of the alignment guide and resection guide, as well as any other instruments, trial components, and implants associated with the desired surgical procedure. It is also recognized, and depicted in FIG. 7, that a lateral approach may be employed, wherein, in part, bone anchor 60 may be implanted in the lateral surface of the distal femur. This will be discussed in more detail, below.

Next, according to the preferred embodiment, alignment guide 10 is placed onto bone anchor 60 by means of aligning cross-bar 63 with slot 64, and sliding bone anchor 60 through passage 21 in base 20. Alignment guide 10 is then locked in position with respect to bone anchor 60 by threadably inserting and advancing a set screw 24 through slot 23 in base 20, until set screw 24 abuts bone anchor 60 to the extent necessary to prevent movement of base 20 relative to bone anchor 60. At this point, collar 30 is free to rotate about base 20.

Resection guide 50 is then attached to collar 30 by inserting attachment rods 51 and 52 into respective channels 45 and 46 in collar 30. Resection guide 50 may then be positioned relative to distal femur 70. As explained above, flexion/extension, varus/valgus and internal/external rotation are attributable to the movement of collar 30 relative to base 20. Proximal/distal orientation is attributable to movement of resection guide 50 relative to collar 30. To simultaneously fix the flexion/extension, varus/valgus and internal/external rotation positions of resection guide 50, with reference to FIG. 3, knob 40 is threadably advanced through aperture 37 in protrusion 34 of collar 30, until threaded shaft 40*b* sufficiently abuts base 20 to lock collar 30 in position relative to base 20. To then lock the proximal/distal position of resection guide 50, knobs 41 and 42 are threadably advanced through bores 38 and 39 respectively until threaded shafts 41*b* and 42*b* respectively, abut rods 51 and 52 of resection guide 50 and lock it in place relative to collar 30. Once the flexion/extension, varus/valgus, internal/external rotation, and proximal/distal orientations of resection guide 50 relative to distal femur 70 are fixed, further procedures known to those of ordinary skill in the art can be carried out in the furtherance of resecting the distal femur 70. For example, surface 80 of guide 50 may be used to guide a saw to form the distal surface of femur 70.

Figure 5:
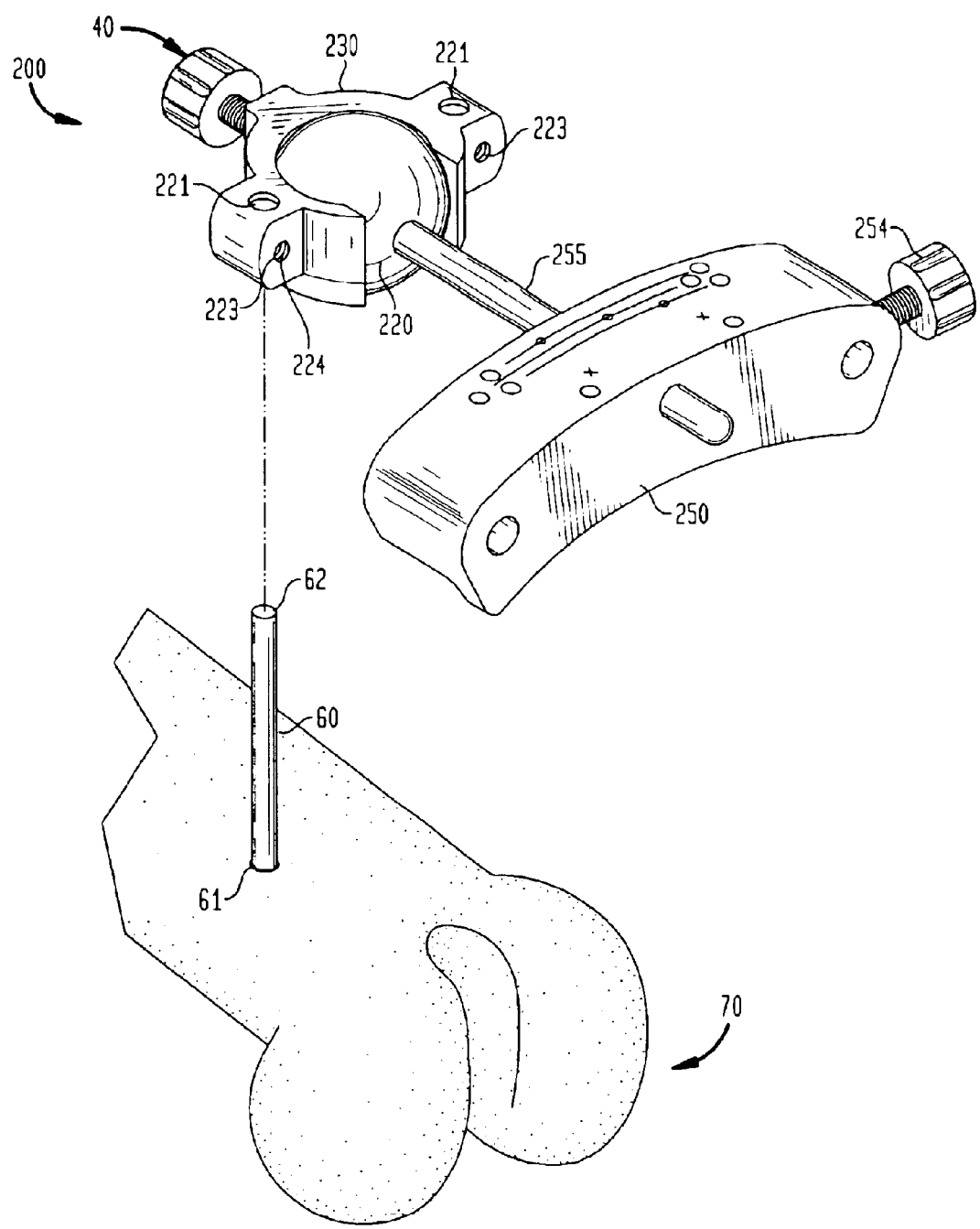
FIG. 5 is a perspective view of a first alternate embodiment of the universal alignment guide where the collar is attachable to the bone anchor.

FIG. 5 illustrates a second embodiment of the universal alignment guide, identified as 200. All other aspects of the preferred and second embodiments being similar, alignment guide 200 primarily differs from alignment guide 10 in that alignment guide 200 is attached to bone anchor 60 at collar 230. Collar 230 has passages 221 which are adapted to accept bone anchor 60. Notably, bone anchor 60 may be coupled to either passage 221 on collar 230 and locked in place. To lock collar 230 against bone anchor 60, a fixator 224, similar to fixator 24 of the preferred embodiment, is threadably engaged and advanced into a threaded slot 223 on collar 230, until fixator 224 abuts bone anchor 60 in passage 221.

In the second embodiment, resection guide 250, comparable to resection guide 50 of the preferred embodiment, is attached to the base 220 of alignment guide 200 via at least one attachment rod 255. Attachment rod 255 is fixedly joined to base 220 and slidably engaged by resection guide 250.

Flexion/extension, varus/valgus and internal/external rotation are attributable to the movement of base 220 within collar 230. In order to fix, or lock, these orientations, actuator 40 is threadably advanced through collar 230 in the same manner as in the preferred embodiment, until it abuts base 220 and locks it in position relative to collar 230.

Proximal/distal orientation is attributable to movement of resection guide 250 along attachment rod 255, relative to base 220. It is further recognized, however, that the single rod attachment to resection guide 250 also facilitates internal/external rotation. In order to lock resection guide 250 against rod 255, there is provided an arrestor 254 that threadably engages resection guide 250, and can be advanced until it abuts rod 255 and locks it into place.

With the exception of accounting for the above-enumerated differences in structure in the second embodiment, the procedure for using resection guide 200 is similar to that of the preferred embodiment. Bone anchor 60 is implanted into a bone, such as distal femur 70, in a variety of orientations such as either anteriorly or laterally. Alignment guide 200 is then set upon bone anchor 60 and locked in position by threadably inserting and advancing fixator 224 in slot 223 in collar 230 until fixator 224 abuts bone anchor 60 to the extent necessary to prevent movement of collar 230 relative to bone anchor 60. At this point, base 220 is free to rotate within collar 230. Then resection guide 250 is slidably set upon attachment rod 225.

To simultaneously fix the flexion/extension, varus/valgus and internal/external rotation positions of resection guide 250, actuator 40 is threadably advanced through collar 230 until it sufficiently abuts base 220 to lock collar 230 in position relative to base 220. To then lock the proximal/distal position of resection guide 250, arrestor 254 is threadably advanced through resection guide 250 until it abut rod 255 and locks it in place relative to base 220. Once the flexion/extension, varus/valgus, internal/external rotation, and proximal/distal orientations of resection guide 250 relative to distal femur 70 are fixed, further procedures known to those of ordinary skill in the art can be carried out in the furtherance of resecting distal femur 70.

Referring to FIGS. 6–8, there is shown another embodiment of a resection guide, particularly a lateral resection guide 100, that may be used with the universal alignment guide of the present invention. With reference to FIG. 6, lateral resection guide 100 has two attachment rods 110 and 112 that are similar to, and perform the same function as, attachment rods 51 and 52 of resection guide 50 in the preferred embodiment, in that they are to interface resection guide 100 with the alignment guide.

As opposed to resection guide 50, however, lateral resection guide 100 is intended for use in the lateral approach to knee replacement surgery, as depicted in FIG. 7. Specifically, this involves inserting bone anchor 60 into the lateral surface 74 of a bone such as the distal femur 70, as opposed to the anterior surface 72 as in the preferred and second embodiments. Notably, it is advantageous to insert bone anchor 60 approximately three inches from the end of the distal femur. Then, coupling alignment guide 10 or 200 to bone anchor 60, attaching lateral resection guide 100 to the alignment guide, and advantageously aligning it to the knee joint as known to those skilled in the art.

Lateral resection guide 100 provides five cutting guide surfaces to facilitate preparing the knee joint for replacement components. Specifically, lateral cutting guide 100 has an anterior cutting guide surface 130, an anterior chamfer cutting guide surface 140, a distal cutting guide surface 150, a posterior chamfer cutting guide surface 160, and a posterior cutting guide surface 170. Additionally, it has features 120, such as holes and slots, to facilitate marking its position and pinning it to bone 70. Because of various anatomical sizes of bones, lateral resection guide 100 may be provided in a variety of sizes, as shown in FIG. 8.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. An alignment guide for positioning an instrument with respect to a bone, comprising:
   a bone anchor having a first end and a second end, and adapted to be attached to a bone at said first end;
   a spheroidal base member mounted on said second end of said bone anchor;
   a collar member mounted on said spheroidal base member; and
   a resection guide attached to said collar member;
   wherein said base member is attached to said second end of said bone anchor; and
   said collar member is associated with said base member facilitate universal motion of said collar member with respect to said base member for positioning said resection guide wherein said spheroidal base member has a passage for cooperative assembly with said second end of said bone anchor.

2. The alignment guide of claim 1 wherein said passage terminates inside said spheroidal base.

3. The alignment guide of claim 1 wherein said base further contains a slot that intersects with said passage, and said alignment guide further comprises a fixator in cooperative assembly with said slot to stabilize said base relative to said bone anchor.

4. The alignment guide of claim 3 wherein said fixator is a set screw and said slot is threaded for cooperative engagement with said set screw.

5. The alignment guide of claim 4 wherein said collar has a window to facilitate manipulating said set screw in said slot.

6. The alignment guide of claim 1 further comprising a motion governor to control motion of said collar relative to said base.

7. The alignment guide of claim 6 wherein said motion governor comprises an aperture in said collar, and an actuator cooperatively assembled with said aperture to control motion of said collar relative to said base.

8. The alignment guide of claim 7 wherein said actuator is a knob having a threaded extension, and said aperture on said collar is threaded for cooperative assembly with said threaded extension of said knob, thus facilitating regulated contact between said knob and said base to control motion of said collar relative to said base.

9. The alignment guide of claim 6 wherein said collar contains at least one channel, and said resection guide contains at least one attachment rod for cooperative assembly with said at least one channel.

10. The alignment guide of claim 9 further comprising at least one arrestor to control motion of said resection guide relative to said collar.

11. The alignment guide of claim 10 wherein said arrestor is a knob having a threaded extension, and said collar contains at least one threaded bore; said at least one threaded bore intersecting said at least one channel of said collar, and available for cooperative engagement by said threaded extension of said knob, thus facilitating regulated contact between said knob and said at least one attachment rod of said resection guide for controlling motion of said resection guide relative to said collar.

12. The alignment guide of claim 6 further comprising
   at least one protrusion on said collar;
   at least one channel in said protrusion;
   said resection guide containing at least one attachment rod; and
   said at least one channel arranged for cooperative assembly with said at least one attachment rod, and at least one arrestor arranged on said alignment guide to control motion of said resection guide relative to said collar.

13. The alignment guide of claim 12 wherein said at least one protrusion has at least one bore oriented at 90° with respect to said at least one channel.

14. The alignment guide of claim 13 wherein said at least one arrestor comprises a knob head attached to a threaded shaft, said shaft extending through said at least one bore into contact with said at least one attachment rod.

15. The alignment guide of claim 1 wherein said collar contains at least one passage for cooperative assembly with said second end of said bone anchor.

16. The alignment guide of claim 1 further comprising a motion governor to control motion of said base relative to said collar.

17. A method of positioning an instrument relative to a bone comprising:
   inserting a bone anchor having a longitudinal axis into an anterior lateral or medial surface of the distal femur, fixedly coupling a spheroidal base to said bone anchor, said spheroidal base having a bore alignable with said bone anchor longitudinal axis for receiving said bone anchor;
   coupling a collar to said spheroidal base in a manner to facilitate universal motion
   attaching a resection guide to said collar; and
   moving said collar with respect to said base to position said resection guide relative to said bone.

18. The method of claim 17 wherein coupling said alignment guide to said bone comprises inserting a bone anchor into an anterior surface of said femur and thereafter attaching said base to said bone anchor.

19. The method of claim 18 wherein coupling said base to said femur comprises laterally inserting a bone anchor into said femur.

20. The method of claim 18 further comprising locking said base in position along said axis of said bone anchor.

21. The method of claim 17 further comprising locking said base to said bone anchor with a locking element mounted on said base.

22. The method of claim 17 wherein attaching said resection guide to said alignment guide comprises attaching said resection guide to said collar of said alignment guide in a manner allowing sliding movement of said resection guide with respect to said collar.

23. The method of claim 22 further comprising positioning said resection guide relative to said collar, and locking said resection guide in place.

24. The method of claim 17 wherein moving said collar to position said resection guide relative to said bone includes moving said collar on said base while having said resection guide attached to said collar.

25. The method of claim 24 further comprising stabilizing said resection guide relative to said bone by locking said collar against said base.

26. The method of claim 17 further comprising providing communication between said collar and a computer navigation system to aid in positioning said resection guide relative to said bone.

27. The method of claim 26 wherein moving said resection guide is based on information received from said computer navigation system.

28. A method for preparing a knee joint surface for placement of a prosthetic implant comprising:
   mounting an alignment guide on an anterior lateral or medial surface of a bone adjacent to a knee joint, said alignment guide comprising a spheroidal base and a collar associated with said base in a manner to facilitate universal motion of said collar with respect to said base;
   fixing said base with respect to said bone by the insertion of an axially extending bone fastener engaging the bone into a bore in said spheroidal base;
   slidably mounting a resection guide on said collar;
   moving said resection guide in at least one of proximal/distal, varus/valgus, flexion/extension or internal/external rotation by moving said collar with respect to said base and said resection guide with respect to said collar to a desired position;
   locking said resection guide in position; and
   resecting said joint surface.

29. The method of claim 28 wherein placing said alignment guide adjacent to said knee joint comprises inserting a bone anchor having a longitudinal axis generally perpendicular tO said bone into a bone and adjusting the position of said base along the axis and locking said base to said bone anchor at a position along an axial extent thereof.

30. The method of claim 29 further comprising locking said base of said alignment guide to said bone anchor with a locking element mounted on said base.

* * * * *

UNITED STATES PATENT AND TRADEMARK OFFICE
CERTIFICATE OF CORRECTION

PATENT NO. : 7,241,298 B2  Page 1 of 1
APPLICATION NO. : 10/356255
DATED : July 10, 2007
INVENTOR(S) : Mark Nemec and Mike Cusick It is certified that error appears in the above-identified patent and that said Letters Patent is hereby corrected as shown below:

Column 1, line 40, "requires" should read --require--.
Column 1, line 55, "is" should read --are--.
Column 2, line 48, "instrumnts" should read --instruments--.
Column 3, line 43, "is" should read --are--.
Column 3, line 64, "are" should read --is--.
Column 4, line 40, "thee" should read --the--.
Column 4, line 41, "contains" should read --contain--.
Column 4, line 54, "protrusion," should read --protrusion--.
Column 4, line 62, "it's" should read --its--.
Column 9, line 17, "abut" should read --abuts--.
Column 9, line 43, "coupling" should read --couple--.
Column 10, line 13, second instance of "member" should read --member to--.
Column 11, line 26, "motion" should read --motion,--.
Column 12, line 40, "tO" should read --to--.

Signed and Sealed this

Twenty-ninth Day of July, 2008

JON W. DUDAS
*Director of the United States Patent and Trademark Office*